United States Patent
Gooding

(10) Patent No.: US 12,213,919 B2
(45) Date of Patent: Feb. 4, 2025

(54) FREE FLOATING PATIENT INTERFACE FOR LASER SURGERY SYSTEM

(71) Applicant: AMO Development, LLC, Irvine, CA (US)

(72) Inventor: Phillip Gooding, Mountain View, CA (US)

(73) Assignee: AMO Development, LLC, Irvine, CA (US)

( * ) Notice: Subject to any disclaimer, the term of this patent is extended or adjusted under 35 U.S.C. 154(b) by 0 days.

(21) Appl. No.: 18/468,640

(22) Filed: Sep. 15, 2023

(65) Prior Publication Data
US 2024/0000611 A1    Jan. 4, 2024

Related U.S. Application Data

(60) Continuation of application No. 17/000,223, filed on Aug. 21, 2020, now Pat. No. 11,759,361, which is a
(Continued)

(51) Int. Cl.
*A61F 9/009*  (2006.01)
*A61F 9/008*  (2006.01)
(Continued)

(52) U.S. Cl.
CPC .......... *A61F 9/009* (2013.01); *A61F 9/00804* (2013.01); *A61F 9/00836* (2013.01);
(Continued)

(58) Field of Classification Search
None
See application file for complete search history.

(56) References Cited

U.S. PATENT DOCUMENTS

| | | |
|---|---|---|
| 3,638,220 A | 1/1972 | Malina et al. |
| 4,436,388 A | 3/1984 | Takahashi et al. |
| (Continued) | | |

FOREIGN PATENT DOCUMENTS

| | | |
|---|---|---|
| CN | 1035566 A | 9/1989 |
| CN | 1154658 A | 7/1997 |
| (Continued) | | |

OTHER PUBLICATIONS

American Heritage Dictionary of the English Language, Definition of Bearing, 2007.

*Primary Examiner* — Carl H Layno
*Assistant Examiner* — Manolis Pahakis

(57) ABSTRACT

A patient interface includes an eye interface device, a scanner, a first support assembly, and a beam source. The eye interface device is configured to interface with an eye of a patient. The scanner is configured to be coupled with the eye interface device and operable to scan an electromagnetic radiation beam in at least two dimensions in an eye interfaced with the eye interface device. The scanner and the eye interface device move in conjunction with movement of the eye. The first support assembly supports the scanner so as to accommodate relative movement between the scanner and the first support assembly parallel so as to accommodate movement of the eye. The beam source generates the electromagnetic radiation beam. The electromagnetic radiation beam propagates from the beam source to the scanner along an optical path having an optical path length that varies in response to movement of the eye.

20 Claims, 8 Drawing Sheets

Related U.S. Application Data division of application No. 14/190,827, filed on Feb. 26, 2014, now Pat. No. 10,751,217.

(60) Provisional application No. 61/780,881, filed on Mar. 13, 2013.

(51) Int. Cl.
*B23K 26/00* (2014.01)
*B23K 26/0622* (2014.01)
*B23K 26/082* (2014.01)
*B23K 26/38* (2014.01)
*B23K 103/00* (2006.01)

(52) U.S. Cl.
CPC ...... *B23K 26/0006* (2013.01); *B23K 26/0624* (2015.10); *B23K 26/082* (2015.10); *B23K 26/38* (2013.01); *A61F 2009/00844* (2013.01); *A61F 2009/00897* (2013.01); *B23K 2103/32* (2018.08); *B23K 2103/50* (2018.08)

(56) References Cited

U.S. PATENT DOCUMENTS

| | | | |
|---|---|---|---|
| 4,443,075 A | | 4/1984 | Crane et al. |
| 4,452,517 A | | 6/1984 | Kohayakawa |
| 4,520,816 A | | 6/1985 | Schachar et al. |
| 4,744,642 A | | 5/1988 | Yoshinaga et al. |
| 4,761,534 A | | 8/1988 | Foulkes |
| 4,964,717 A | | 10/1990 | Koester |
| 5,090,797 A | * | 2/1992 | Cleveland ............... A61B 3/113 359/872 |
| 5,094,523 A | | 3/1992 | Reznichenko et al. |
| 5,226,903 A | | 7/1993 | Mizuno |
| 5,305,759 A | | 4/1994 | Kaneko et al. |
| 5,336,215 A | | 8/1994 | Hsueh et al. |
| 5,360,424 A | * | 11/1994 | Klopotek ............ A61F 9/00802 606/4 |
| 5,364,390 A | * | 11/1994 | Taboada ............. B23K 26/0648 606/4 |
| 5,445,633 A | | 8/1995 | Nakamura et al. |
| 5,446,547 A | | 8/1995 | Guenther et al. |
| 5,459,325 A | * | 10/1995 | Hueton ............ G01N 27/44721 204/461 |
| 5,493,109 A | | 2/1996 | Wei et al. |
| 5,501,226 A | | 3/1996 | Petersen et al. |
| 5,549,632 A | | 8/1996 | Lai |
| 5,582,752 A | | 12/1996 | Zair |
| 5,586,981 A | | 12/1996 | Hu |
| 5,618,285 A | | 4/1997 | Zair |
| 5,688,262 A | | 11/1997 | Abraham |
| 5,709,677 A | | 1/1998 | Slatkine |
| 5,720,894 A | | 2/1998 | Neev et al. |
| 5,782,822 A | | 7/1998 | Telfair et al. |
| 5,870,167 A | | 2/1999 | Knopp et al. |
| 5,880,880 A | | 3/1999 | Anderson et al. |
| 5,923,399 A | | 7/1999 | Van De Velde |
| 5,957,915 A | | 9/1999 | Trost |
| 5,973,781 A | | 10/1999 | Moeller et al. |
| 5,984,916 A | | 11/1999 | Lai |
| 6,004,314 A | | 12/1999 | Wei et al. |
| 6,019,472 A | | 2/2000 | Koester et al. |
| 6,095,648 A | | 8/2000 | Birngruber et al. |
| 6,099,522 A | * | 8/2000 | Knopp ............... A61F 9/00804 606/5 |
| 6,201,608 B1 | | 3/2001 | Mandella et al. |
| 6,261,220 B1 | | 7/2001 | Frey et al. |
| 6,271,915 B1 | | 8/2001 | Frey et al. |
| 6,287,298 B1 | | 9/2001 | Nighan et al. |
| 6,322,216 B1 | | 11/2001 | Yee et al. |
| 6,454,761 B1 | | 9/2002 | Freedman |
| 6,460,997 B1 | | 10/2002 | Frey et al. |
| 6,475,138 B1 | | 11/2002 | Schechter et al. |
| 6,488,676 B1 | | 12/2002 | Glockler et al. |
| 6,563,781 B2 | | 5/2003 | Hasegawa et al. |
| 6,585,725 B1 | | 7/2003 | Mukai |
| 6,824,540 B1 | | 11/2004 | Lin |
| 6,942,656 B2 | | 9/2005 | Pawlowski et al. |
| 7,036,934 B1 | | 5/2006 | Youssefi et al. |
| 7,158,226 B2 | | 1/2007 | Gfroerer et al. |
| 7,278,989 B2 | | 10/2007 | Vinciguerra et al. |
| 7,364,296 B2 | | 4/2008 | Miller et al. |
| 7,551,293 B2 | | 6/2009 | Yelin et al. |
| 7,621,637 B2 | | 11/2009 | Rathjen et al. |
| 7,648,242 B2 | | 1/2010 | Ferguson et al. |
| 7,655,002 B2 | | 2/2010 | Myers et al. |
| 7,717,907 B2 | | 5/2010 | Ruiz et al. |
| 7,766,903 B2 | | 8/2010 | Blumenkranz et al. |
| 7,911,670 B2 | | 3/2011 | Bec et al. |
| 7,982,879 B2 | | 7/2011 | Desjardins et al. |
| 8,175,685 B2 | | 5/2012 | Yun et al. |
| 8,182,472 B2 | | 5/2012 | Yee |
| 8,262,646 B2 | | 9/2012 | Frey et al. |
| 8,350,183 B2 | | 1/2013 | Vogel et al. |
| 8,382,745 B2 | | 2/2013 | Naranjo-Tackman et al. |
| 8,414,564 B2 | | 4/2013 | Goldshleger et al. |
| 8,568,393 B2 | | 10/2013 | Palanker |
| 8,702,770 B2 | | 4/2014 | Hanft et al. |
| 8,912,511 B2 | | 12/2014 | Schoenborn |
| 8,995,477 B2 | | 3/2015 | Amano |
| 9,044,304 B2 | | 6/2015 | Raksi et al. |
| 10,470,932 B2 | | 11/2019 | Gooding et al. |
| 11,478,380 B2 | | 10/2022 | Schuele et al. |
| 11,534,340 B2 | | 12/2022 | Gooding et al. |
| 2001/0010003 A1 | | 7/2001 | Lai |
| 2001/0037105 A1 | | 11/2001 | Lin |
| 2002/0007176 A1 | | 1/2002 | Campin et al. |
| 2002/0048025 A1 | | 4/2002 | Takaoka |
| 2002/0080359 A1 | | 6/2002 | Denk et al. |
| 2002/0082466 A1 | | 6/2002 | Han |
| 2002/0198516 A1 | | 12/2002 | Knopp et al. |
| 2003/0090772 A1 | * | 5/2003 | Karin ............... G02B 26/101 359/223.1 |
| 2003/0208189 A1 | | 11/2003 | Payman |
| 2004/0012666 A1 | | 1/2004 | Sasaki |
| 2004/0070822 A1 | | 4/2004 | Shioda et al. |
| 2004/0075879 A1 | | 4/2004 | Karin |
| 2004/0078030 A1 | | 4/2004 | Lin |
| 2004/0081341 A1 | | 4/2004 | Cherek et al. |
| 2004/0143246 A1 | | 7/2004 | Maeda et al. |
| 2004/0223385 A1 | | 11/2004 | Fleming et al. |
| 2004/0243112 A1 | | 12/2004 | Bendett et al. |
| 2004/0254568 A1 | | 12/2004 | Rathjen |
| 2004/0262440 A1 | | 12/2004 | Ziavras et al. |
| 2005/0043597 A1 | | 2/2005 | Xie |
| 2005/0211872 A1 | | 9/2005 | Kawano et al. |
| 2005/0228366 A1 | | 10/2005 | Kessler et al. |
| 2005/0231727 A1 | | 10/2005 | Podoleanu et al. |
| 2006/0084956 A1 | | 4/2006 | Sumiya |
| 2006/0106371 A1 | | 5/2006 | Muhlhoff et al. |
| 2006/0129141 A1 | | 6/2006 | Lin |
| 2006/0170930 A1 | | 8/2006 | Li |
| 2006/0187462 A1 | | 8/2006 | Srinivasan et al. |
| 2006/0195076 A1 | | 8/2006 | Blumenkranz et al. |
| 2006/0217688 A1 | | 9/2006 | Lai |
| 2006/0259021 A1 | | 11/2006 | Lin |
| 2007/0002277 A1 | | 1/2007 | Hanebuchi |
| 2007/0010804 A1 | * | 1/2007 | Rathjen ................. A61B 90/50 606/5 |
| 2007/0032782 A1 | | 2/2007 | Youssefi et al. |
| 2007/0059205 A1 | | 3/2007 | Ganz et al. |
| 2007/0093798 A1 | | 4/2007 | Debenedictis et al. |
| 2007/0109497 A1 | * | 5/2007 | Chang ................ A61B 3/14 351/205 |
| 2007/0129709 A1 | | 6/2007 | Andersen et al. |
| 2007/0291277 A1 | | 12/2007 | Everett et al. |
| 2008/0015553 A1 | | 1/2008 | Zacharias |
| 2008/0033406 A1 | | 2/2008 | Andersen et al. |
| 2008/0081950 A1 | | 4/2008 | Koenig et al. |
| 2008/0082078 A1 | | 4/2008 | Berlin |
| 2008/0088938 A1 | | 4/2008 | Lai |
| 2008/0100848 A1 | | 5/2008 | Kobayashi |
| 2008/0167642 A1 | | 7/2008 | Palanker et al. |

(56) References Cited

U.S. PATENT DOCUMENTS

| | | |
|---|---|---|
| 2008/0218691 A1 | 9/2008 | Fercher |
| 2008/0231803 A1 | 9/2008 | Feldon et al. |
| 2008/0231808 A1* | 9/2008 | Van .................. A61B 3/1025 351/221 |
| 2008/0243107 A1 | 10/2008 | Muhlhoff et al. |
| 2008/0278687 A1 | 11/2008 | Somani |
| 2009/0067042 A1 | 3/2009 | Tanikawa et al. |
| 2009/0143772 A1 | 6/2009 | Kurtz |
| 2009/0149726 A1 | 6/2009 | Hyde et al. |
| 2009/0171327 A1* | 7/2009 | Kurtz .................... A61F 9/009 606/6 |
| 2009/0187176 A1 | 7/2009 | Assa et al. |
| 2009/0230269 A1* | 9/2009 | Dallarosa ............ F16M 11/12 248/299.1 |
| 2009/0247997 A1 | 10/2009 | Watanabe et al. |
| 2009/0279052 A1* | 11/2009 | Hauger .................. G01B 9/04 351/208 |
| 2009/0299347 A1 | 12/2009 | Vogler et al. |
| 2010/0042081 A1 | 2/2010 | Rathjen |
| 2010/0067020 A1 | 3/2010 | Podoleanu et al. |
| 2010/0069894 A1 | 3/2010 | Mrochen et al. |
| 2010/0076417 A1 | 3/2010 | Suckewer et al. |
| 2010/0082017 A1 | 4/2010 | Zickler et al. |
| 2010/0089884 A1* | 4/2010 | Sercel ................ B23K 26/066 219/121.72 |
| 2010/0130968 A1 | 5/2010 | Vogler |
| 2010/0165289 A1 | 7/2010 | Nozato et al. |
| 2010/0204578 A1* | 8/2010 | Schmidt ............. A61B 8/4281 600/443 |
| 2010/0256614 A1 | 10/2010 | Donitzky et al. |
| 2010/0290007 A1 | 11/2010 | Van De Velde |
| 2011/0001930 A1 | 1/2011 | Levecq |
| 2011/0028951 A1 | 2/2011 | Raksi et al. |
| 2011/0028958 A1 | 2/2011 | Raksi et al. |
| 2011/0058175 A1 | 3/2011 | Suehira |
| 2011/0118713 A1 | 5/2011 | Raksi |
| 2011/0134436 A1 | 6/2011 | Podoleanu et al. |
| 2011/0152845 A1 | 6/2011 | Hammer et al. |
| 2011/0172649 A1 | 7/2011 | Schuele et al. |
| 2011/0184395 A1 | 7/2011 | Schuele et al. |
| 2011/0218523 A1 | 9/2011 | Robl |
| 2011/0234975 A1 | 9/2011 | Hirose |
| 2011/0245814 A1* | 10/2011 | Taboada ................ A61F 9/008 606/4 |
| 2011/0309231 A1 | 12/2011 | Cooper et al. |
| 2011/0310395 A1 | 12/2011 | Tsai et al. |
| 2011/0319873 A1 | 12/2011 | Raksi et al. |
| 2011/0319875 A1 | 12/2011 | Loesel et al. |
| 2012/0029491 A1* | 2/2012 | Rathjen ................ A61F 9/008 606/4 |
| 2012/0029492 A1* | 2/2012 | Rathjen .............. A61F 9/00836 606/5 |
| 2012/0078241 A1 | 3/2012 | Gooding et al. |
| 2012/0140170 A1 | 6/2012 | Hirose et al. |
| 2012/0218515 A1 | 8/2012 | Imamura |
| 2012/0271286 A1* | 10/2012 | Curatu ............... G02B 13/0005 606/4 |
| 2012/0283708 A1 | 11/2012 | Raksi et al. |
| 2013/0050649 A1 | 2/2013 | Juhasz et al. |
| 2013/0072917 A1* | 3/2013 | Kaschke ............ A61F 9/00736 606/6 |
| 2013/0085483 A1 | 4/2013 | Rathjen |
| 2013/0103014 A1 | 4/2013 | Gooding et al. |
| 2013/0120710 A1 | 5/2013 | Buckland et al. |
| 2013/0120711 A1 | 5/2013 | Hacker et al. |
| 2013/0131653 A1 | 5/2013 | Huang |
| 2013/0132653 A1 | 5/2013 | Post et al. |
| 2013/0158530 A1 | 6/2013 | Goldshleger et al. |
| 2013/0169931 A1 | 7/2013 | Lee et al. |
| 2013/0226157 A1 | 8/2013 | Huang |
| 2013/0226160 A1 | 8/2013 | Rathjen et al. |
| 2013/0261612 A1 | 10/2013 | Yokosuka et al. |
| 2013/0310816 A1* | 11/2013 | Rathjen .................. A61F 9/008 606/4 |
| 2014/0046306 A1 | 2/2014 | Huang et al. |
| 2014/0046308 A1 | 2/2014 | Bischoff et al. |
| 2014/0107634 A1 | 4/2014 | Vogler et al. |
| 2014/0114294 A1 | 4/2014 | Heitel |
| 2014/0121508 A1 | 5/2014 | Latimer et al. |
| 2014/0128821 A1 | 5/2014 | Gooding et al. |
| 2014/0128852 A1* | 5/2014 | Gooding ................ A61F 9/008 606/4 |
| 2014/0163534 A1 | 6/2014 | Angeley et al. |
| 2014/0180265 A1 | 6/2014 | Huang |
| 2014/0240674 A1 | 8/2014 | Wei et al. |
| 2014/0257259 A1 | 9/2014 | Papastathopoulos et al. |
| 2014/0276671 A1 | 9/2014 | Gooding |
| 2014/0313315 A1 | 10/2014 | Shoham et al. |
| 2014/0316389 A1 | 10/2014 | Schuele et al. |
| 2014/0330260 A1* | 11/2014 | Bergt ................ B23K 26/082 606/5 |
| 2015/0116660 A1* | 4/2015 | Matsumoto .......... A61B 3/0058 351/206 |
| 2015/0202083 A1 | 7/2015 | Takeda et al. |
| 2016/0040976 A1 | 2/2016 | Berkeley et al. |
| 2016/0081851 A1 | 3/2016 | Huang |
| 2016/0106581 A1 | 4/2016 | Gonzalez et al. |
| 2016/0106582 A1 | 4/2016 | Campos et al. |
| 2016/0161244 A1 | 6/2016 | Jaillon et al. |
| 2016/0235588 A1 | 8/2016 | Hart et al. |
| 2017/0000647 A1 | 1/2017 | Schuele et al. |
| 2023/0084131 A1 | 3/2023 | Schuele et al. |

FOREIGN PATENT DOCUMENTS

| | | |
|---|---|---|
| JP | H06277248 A | 10/1994 |
| JP | H06291399 A | 10/1994 |
| JP | H11192253 A | 7/1999 |
| JP | 2000060893 A | 2/2000 |
| JP | 2000139996 A | 5/2000 |
| JP | 2000152954 A | 6/2000 |
| JP | 2008149164 A | 7/2008 |
| JP | 2008534993 A | 8/2008 |
| WO | 9308877 A1 | 5/1993 |
| WO | 2008098381 A1 | 8/2008 |
| WO | 2011094758 A2 | 8/2011 |
| WO | 2011147570 A1 | 12/2011 |
| WO | 2012135579 A2 | 10/2012 |
| WO | 2014158615 A1 | 10/2014 |

* cited by examiner using the base assembly to support a third reflector configured to reflect the electromagnetic radiation beam to propagate parallel to the third direction and to be incident on the second reflector - 116 operating the scanner to scan the electromagnetic radiation beam in at least two dimensions - 118 focusing the electromagnetic radiation beam to a focal point - 120 operating the scanner to scan the focal point in three dimensions - 122 inhibiting at least one of (1) gravity-induced movement of the scanner in the vertical direction and (2) transfer of gravity-induced force to the patient - 124 monitoring a relative position of at least one of the group consisting of (1) between the scanner and the first support assembly, (2) between the first support assembly and the second support assembly, and (3) between the second support assembly and the base assembly - 126 inhibiting relative movement during positioning of the scanner relative to the patient between at least one of (1) the scanner and the first support assembly, (2) the first support assembly and the second support assembly, and (3) the second support assembly and the base assembly - 128

*FIG. 4* using a second support assembly to support the first support assembly so as to accommodate relative movement between the first support assembly and the second support assembly so as to accommodate patient movement - *208* using the first support assembly to support a first reflector configured to reflect the electromagnetic radiation beam so as to propagate to the scanner along a portion of the optical path - *210* using a base assembly to support the second support assembly so as to accommodate relative movement between the second support assembly and the base assembly so as to accommodate patient movement - *212* using the second support assembly to support a second reflector configured to reflect the electromagnetic radiation beam to propagate along a portion of the optical path so as to be incident on the first reflector - *214* using the base assembly to support a third reflector configured to reflect the electromagnetic radiation beam to propagate along a portion of the optical path so as to be incident on the second reflector - *216* monitoring at least one of a relative position and a relative orientation of at least one of the group consisting of (1) between the scanner and the first support assembly, (2) between the first support assembly and the second support assembly, and (3) between the second support assembly and the base assembly - *218* inhibiting relative movement during positioning of the scanner relative to the patient between at least one of (1) the scanner and the first support assembly, (2) the first support assembly and the second support assembly, and (3) the second support assembly and the base assembly - *220*

*FIG. 6B* excellent# FREE FLOATING PATIENT INTERFACE FOR LASER SURGERY SYSTEM

CROSS-REFERENCES TO RELATED APPLICATIONS

This application claims priority to and is a continuation of U.S. patent application Ser. No. 17/000,223, filed Aug. 21, 2020, now U.S. Pat. No. 11,759,361, which claims priority to and is a divisional of U.S. patent application Ser. No. 14/190,827, filed Feb. 26, 2014, now U.S. Pat. No. 10,751,217, which claims priority to U.S. provisional application No. 61/780,881 filed on Mar. 13, 2013, the entire contents of which are incorporated herein by reference.

FIELD OF THE INVENTION

Laser eye surgery systems have become ubiquitous and varied in purpose. For example, a laser eye surgery system may be configured to reshape the anterior surface of the cornea via ablation to effect a refractive correction. A laser eye surgery system may also be configured to create a corneal flap to expose an underlying portion of the cornea such that the underlying portion can be reshaped via ablation and then recovered with the flap. More recently developed laser eye surgery systems may be configured to create one or more incisions in the cornea or limbus to reshape the cornea, create one or more incisions in the cornea to provide access for a cataract surgical instrument and/or to provide access for implantation of an intraocular lens, incise a capsulotomy in the anterior lens capsule to provide access for removal of a cataractous lens, segment a cataractous lens, and/or incise a capsulotomy in the posterior lens capsule opening.

Many laser eye surgery systems generate a series of laser beam pulses via a laser beam source. The laser beam pulses propagate along an optical path to the patient's eye. The optical path typically includes controllable elements such as scanning mechanisms and/or focusing mechanisms to control the direction and/or location of the emitted laser beam pulses relative to the patient.

Some laser eye surgery systems are configured to track eye movement (e.g., change of viewing direction of the eye) such that control over the direction and/or location of the emitted laser beam pulses can be accomplished so as to account for the eye movement. For example, a laser eye surgery system may optically track a feature in the eye, such as a natural feature or a fiduciary marker added to the eye, so as to track movement of the eye.

In contrast, other laser eye surgery systems may be configured to inhibit eye movement. For example, a contact lens may be employed that directly contacts the anterior surface of the cornea so as to restrain eye movement. Such restraint, however, may cause associated patient discomfort and/or anxiety.

Beyond eye movement, many laser eye surgery systems are configured to inhibit relative movement between the patient and the laser eye surgery system. For example, a laser eye surgery system may include some sort of substantial patient restraint feature such as a dedicated support assembly (e.g., chair or bed), which can include restraint features configured to inhibit movement of the patient relative to the support assembly. Such a dedicated support assembly may include a positioning mechanism by which the patient can be moved to suitably position the patient's eye relative to the optical path of the laser eye surgery system. Additionally, a laser eye surgery system may be configured to rigidly support components that determine the location of the optical path of the laser pulses so as to substantially prevent movement of the optical path relative to the dedicated support assembly, thereby also inhibiting relative movement of the patient's eye relative to the emitted laser pulses. A dedicated support assembly and rigid support of optical path components, however, can add significant complexity and related cost to a laser eye surgery system. Additionally, the use of rigid support of optical path components and a dedicated patient support assembly can fail to preclude the possibility of some level of significant relative movement between the patient and the laser eye surgery system.

Thus, laser surgery systems with improved characteristics with respect to patient movement, and related methods, may be beneficial.

SUMMARY

Patient interface assemblies and related methods are provided that can be used in suitable laser surgery systems such as, for example, laser eye surgery systems. In many embodiments, a patient interface assembly is configured to accommodate relative movement of a patient while maintaining alignment between a scanned electromagnetic treatment beam and the patient. By accommodating movement of the patient, additional system complexity and related cost associated with attempting to restrain movement of the patient can be avoided. Additionally, accommodation of movement of the patient can be employed to increase ease of use of a laser surgery system, such as by configuring the laser surgery system to be supported by a repositionable cart that can be moved adjacent to an existing patient support assembly (e.g., a non-dedicated patient support assembly such as a bed).

Thus, in one aspect, a method of accommodating patient movement in a laser surgery system is provided. The method includes using a first support assembly to support a scanner so as to accommodate relative translation between the scanner and the first support assembly parallel to a first direction. The scanner is operable to controllably scan an electromagnetic radiation beam and configured to be coupled with a patient so that the scanner moves in conjunction with movement of the patient. A second support assembly is used to support the first support assembly so as to accommodate relative translation between the first support assembly and the second support assembly parallel to a second direction that is transverse to the first direction. A base assembly is used to support the second support assembly so as to accommodate relative translation between the second support assembly and the base assembly parallel to a third direction that is transverse to each of the first and second directions. The electromagnetic radiation beam is propagated in a direction that is fixed relative to the base assembly. The first support assembly is used to support a first reflector configured to reflect the electromagnetic radiation beam so as to propagate parallel to the first direction and to the scanner. The second support assembly is used to support a second reflector configured to reflect the electromagnetic radiation beam so as to propagate parallel to the second direction and to be incident on the first reflector. Relative translation between the scanner and the first assembly, between the first assembly and the second assembly, and between the second assembly and the base assembly is used to accommodate three-dimensional relative translation between the scanner and the base assembly.

In many embodiments of the method, the scanner has particular operational characteristics relative to the electromagnetic radiation beam. For example, the scanner can be operable to scan the electromagnetic radiation beam in at least two dimensions. The scanner can be operable to focus the electromagnetic radiation beam to a focal point. The scanner can be operable to scan the focal point in three dimensions.

In many embodiments of the method, the second direction is perpendicular to the first direction and the third direction is perpendicular to each of the first and second directions. One of the first, second, and third directions can be vertically oriented. For example, the third direction can be vertically oriented and each of the first and second directions can be horizontally oriented. The method can include inhibiting at least one of (1) gravity-induced movement of the scanner in the vertical direction and (2) transfer of gravity-induced force to the patient.

In many embodiments of the method, the electromagnetic radiation beam includes a series of laser pulses. The laser pulses can be configured to modify eye tissue.

The method can include using the base assembly to support a third reflector. The third reflector can be configured to reflect the electromagnetic radiation beam to propagate parallel to the third direction and to be incident on the second reflector.

The method can include monitoring one or more relative positions between components. For example, the method can include monitoring a relative position of at least one of the group consisting of (1) between the scanner and the first support assembly, (2) between the first support assembly and the second support assembly, and (3) between the second support assembly and the base assembly.

The method can include inhibiting relative movement during positioning of the scanner relative to the patient between at least one of (1) the scanner and the first support assembly, (2) the first support assembly and the second support assembly, and (3) the second support assembly and the base assembly. Such inhibiting relative movement during positioning of the scanner relative to the patient can be used to ensure that adequate relative movement ranges are available after the scanner is positioned relative to the patient.

In another aspect, a patient interface assembly for a laser eye surgery system is provided. The patient interface assembly includes an eye interface device, a scanner, a first support assembly, a second support assembly, a base assembly, a beam source, a first reflector, and a second reflector. The eye interface is configured to interface with an eye of a patient. The scanner is coupled with the eye interface and operable to scan an electromagnetic radiation beam in at least two dimensions in an eye interfaced with the eye interface device. The scanner and the eye interface move in conjunction with movement of the eye. The first support assembly supports the scanner so as to accommodate relative translation between the scanner and the first support assembly parallel to a first direction. The second support assembly supports the first support assembly so as to accommodate relative translation between the first support assembly and the second support assembly parallel to a second direction that is transverse to the first direction. The base assembly supports the second support assembly so as to accommodate relative translation between the second support assembly and the base assembly parallel to a third direction. The third direction is transverse to each of the first and second directions. The beam source generates the electromagnetic radiation beam and outputs the electromagnetic radiation beam so as to propagate in a fixed direction relative to the base assembly. The first reflector is supported by the first support assembly and configured to reflect the electromagnetic radiation beam to propagate parallel to the first direction and propagate to the scanner. The second reflector is supported by the second support assembly and configured to reflect the electromagnetic radiation beam to propagate parallel to the second direction and to be incident on the first reflector. Relative translation between the scanner and the first assembly, between the first assembly and the second assembly, and between the second assembly and the base assembly accommodates three-dimensional relative translation between the eye interface and the base assembly.

The patient interface assembly can include an objective lens assembly disposed between the scanner and the eye interface. For example, the electromagnetic radiation beam can propagate from the scanner to pass through the objective lens assembly and then from the objective lens assembly through the eye interface.

In many embodiments of the patient interface assembly, the electromagnetic radiation beam is focused to a focal point. The scanner can be operable to scan the focal point in three dimensions in an eye interfaced with the eye interface device.

In many embodiments of the patient interface assembly, the scanner includes a z-scan device and an xy-scan device. The z-scan device can be operable to change a depth of the focal point in the eye. The xy-scan device can be operable to scan the focal point in two dimensions transverse to the propagation direction of the electromagnetic radiation beam.

In many embodiments of the patient interface assembly, the second direction is perpendicular to the first direction and the third direction is perpendicular to each of the first and second directions. One of the first, second, and third directions can be vertically oriented. The patient interface assembly can include a counter-balance mechanism coupled with the scanner and configured to inhibit at least one of (1) gravity-induced movement of the eye interface in the vertical direction and (2) transfer of gravity-induced force to an eye coupled with the eye interface device. The third direction can be vertically oriented and each of the first and second directions can be horizontally oriented.

The patient interface assembly can include at least one sensor to monitor relative position between components of the patient interface assembly. For example, the patient interface assembly can include at least one sensor configured to monitor relative position of at least one of the group consisting of between the scanner and the first support assembly, between the first support assembly and the second support assembly, and between the second support assembly and the base assembly.

In many embodiments of the patient interface assembly, the electromagnetic radiation beam includes a series of laser pulses. The laser pulses can be configured to modify eye tissue.

The patient interface assembly can include at least one device (e.g., one or more solenoid brake assemblies, one or more detent mechanisms, or any other suitable mechanism configured to selectively inhibit relative movement between components coupled for relative movement) configured to inhibit relative movement during positioning of the scanner relative to the patient between at least one of (1) the scanner and the first support assembly, (2) the first support assembly and the second support assembly, and (3) the second support assembly and the base assembly. Such a device(s) can be used to ensure that adequate relative movement ranges are available after the scanner is positioned relative to the patient.

In many embodiments, the patient interface assembly includes a third reflector supported by the base assembly. The third reflector is configured to reflect the electromagnetic radiation beam to propagate parallel to the third direction and to be incident on the second reflector.

In another aspect, a method of accommodating patient movement in a laser surgery system is provided. The method includes using a using a first support assembly to support a scanner so as to accommodate relative movement between the scanner and the first support assembly so as to accommodate patient movement. The scanner is operable to controllably scan an electromagnetic radiation beam and configured to be coupled with a patient so that the scanner moves in conjunction with movement of the patient. The method further includes using a beam source to generate the electromagnetic radiation beam. The method further includes propagating the electromagnetic radiation beam from the beam source to the scanner along an optical path having an optical path length that changes in response to patient movement.

The method can include further acts related to the optical path. For example, the method can include using a second support assembly to support the first support assembly so as to accommodate relative movement between the first support assembly and the second support assembly so as to accommodate patient movement. The method can include using the first support assembly to support a first reflector configured to reflect the electromagnetic radiation beam so as to propagate to the scanner along a portion of the optical path. The method can include using a base assembly to support the second support assembly so as to accommodate relative movement between the second support assembly and the base assembly so as to accommodate patient movement. The method can include using the second support assembly to support a second reflector configured to reflect the electromagnetic radiation beam to propagate along a portion of the optical path so as to be incident on the first reflector. The method can include using the base assembly to support a third reflector configured to reflect the electromagnetic radiation beam to propagate along a portion of the optical path so as to be incident on the second reflector.

The method can include the use of relative translation and/or relative rotation between optical path related components. For example, the relative movement between the scanner and the first support assembly can be a translation in a first direction. The relative movement between the first support assembly and the second support assembly can be a translation in a second direction that is transverse to the first direction. The relative movement between the second support assembly and the base assembly can be a translation in a third direction that is transverse to each of the first and second directions. The second direction can be perpendicular to the first direction. The third direction can be perpendicular to each of the first and second directions. At least one of (1) the relative movement between the scanner and the first support assembly, (2) the relative movement between the first support assembly and the second support assembly, and (3) the relative movement between the second support assembly and the base assembly can be a relative rotation.

The method can include inhibiting at least one of (1) gravity-induced movement of the scanner in the vertical direction and (2) transfer of gravity-induced force to the patient. One of the first, second, and third directions can be vertically oriented. For example, the third direction can be vertically oriented and each of the first and second directions can be horizontally oriented.

The scanner can be operable to scan any suitable electromagnetic radiation beam in any suitable fashion. For example, the scanner can be operable to scan the electromagnetic radiation beam in at least two dimensions. The scanner can be operable to focus the electromagnetic radiation beam to a focal point and scan the focal point in three dimensions. The scanner can be configured to be coupled with an eye of the patient and to controllably scan a focal point of the electromagnetic radiation beam within a tissue of the eye. The electromagnetic radiation beam can include a series of laser pulses configured to modify eye tissue.

The method can include monitoring relative position and/or relative orientation between optical path related components. For example, the method can include monitoring at least one of a relative position and a relative orientation of at least one of the group consisting of (1) between the scanner and the first support assembly, (2) between the first support assembly and the second support assembly, and (3) between the second support assembly and the base assembly.

The method can include inhibiting relative movement between optical path related components during positioning of the scanner relative to the patient. For example, the method can include inhibiting relative movement during positioning of the scanner relative to the patient between at least one of (1) the scanner and the first support assembly, (2) the first support assembly and the second support assembly, and (3) the second support assembly and the base assembly.

In another aspect, a patient interface assembly for a laser eye surgery system is provided. The patient interface assembly includes an eye interface device, a scanner, a first support assembly, and beam source. The eye interface device is configured to interface with an eye of a patient. The scanner is configured to be coupled with the eye interface device and operable to scan an electromagnetic radiation beam in at least two dimensions in an eye interfaced with the eye interface device. The scanner and the eye interface device move in conjunction with movement of the eye. The first support assembly supports the scanner so as to accommodate relative movement between the scanner and the first support assembly parallel so as to accommodate movement of the eye. The beam source generates the electromagnetic radiation beam. The electromagnetic radiation beam propagates from the beam source to the scanner along an optical path having an optical path length that varies in response to movement of the eye.

The patient interface assembly can include additional optical path related components. For example, the patient interface assembly can include a second support assembly that supports the first support assembly so as to accommodate relative movement between the first support assembly and the second support assembly so as to accommodate movement of the eye. The patient interface assembly can include a first reflector supported by the first support assembly and configured to reflect the electromagnetic radiation beam to propagate to the scanner along a portion of the optical path. The patient interface assembly can include a base assembly that supports the second support assembly so as to accommodate relative movement between the second support assembly and the base assembly so as to accommodate movement of the eye. The patient interface assembly can include a second reflector supported by the second support assembly and configured to reflect the electromagnetic radiation beam to propagate along a portion of the optical path so as to be incident on the first reflector. The patient interface assembly can include a third reflector supported by the base assembly and configured to reflect the electromagnetic radiation beam to propagate along a portion of the optical path so as to be incident on the second reflector.

The patient interface assembly can employ relative translation and/or relative rotation between optical path related components. For example, the relative movement between the scanner and the first support assembly can be a translation in a first direction. The relative movement between the first support assembly and the second support assembly can be a translation in a second direction that is transverse to the first direction. The relative movement between the second support assembly and the base assembly can be a translation in a third direction that is transverse to each of the first and second directions. The second direction can be perpendicular to the first direction. The third direction can be perpendicular to each of the first and second directions. At least one of (1) the relative movement between the scanner and the first support assembly, (2) the relative movement between the first support assembly and the second support assembly, and (3) the relative movement between the second support assembly and the base assembly can be a relative rotation.

The patient interface assembly can include a counterbalance mechanism configured to inhibit at least one of (1) gravity-induced movement of the scanner in the vertical direction and (2) transfer of gravity-induced force to eye of the patient. The third direction can be vertically oriented and each of the first and second directions can be horizontally oriented.

The scanner of the patient interface assembly can be operable to scan any suitable electromagnetic radiation beam in any suitable fashion. For example, the scanner can be operable to scan the electromagnetic radiation beam in at least two dimensions. The scanner can be operable to focus the electromagnetic radiation beam to a focal point and scan the focal point in three dimensions. The scanner can be configured to be coupled with an eye of the patient and to controllably scan a focal point of the electromagnetic radiation beam within a tissue of the eye. The electromagnetic radiation beam can include a series of laser pulses configured to modify eye tissue. The scanner can include a z-scan device and an xy-scan device. The z-scan device can be operable to change a depth of the focal point in the eye. The xy-scan device can be operable to scan the focal point in two dimensions transverse to the propagation direction of the electromagnetic radiation beam.

The patient interface assembly can include other suitable optical path related components. For example, the patient interface assembly can include at least one sensor configured to monitor relative position of at least one of the group consisting of (1) between the scanner and the first support assembly, (2) between the first support assembly and the second support assembly, and (3) between the second support assembly and the base assembly. The patient interface assembly can include an objective lens assembly disposed between and coupled with the scanner and the eye interface device. The electromagnetic radiation beam can propagate from the scanner to pass through the objective lens assembly and then from the objective lens assembly through the eye interface device. The patient interface assembly can include at least one device (e.g., one or more solenoid brake assemblies, one or more detent mechanisms, or any other suitable mechanism configured to selectively inhibit relative movement between components coupled for relative movement) configured to inhibit relative movement during positioning of the scanner relative to the patient between at least one of (1) the scanner and the first support assembly, (2) the first support assembly and the second support assembly, and (3) the second support assembly and the base assembly. Such a device(s) can be used to ensure that adequate relative movement ranges are available after the scanner is positioned relative to the patient.

For a fuller understanding of the nature and advantages of the present invention, reference should be made to the ensuing detailed description and accompanying drawings. Other aspects, objects and advantages of the invention will be apparent from the drawings and detailed description that follows.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4 is a simplified block diagram of optional acts, in accordance with many embodiments, that can be accomplished in the method of FIG. 3.

FIG. 6B is a simplified block diagram of optional acts, in accordance with many embodiments, that can be accomplished in the method of FIG. 6A.

DETAILED DESCRIPTION

In the following description, various embodiments of the present invention will be described. For purposes of explanation, specific configurations and details are set forth in order to provide a thorough understanding of the embodiments. It will also, however, be apparent to one skilled in the art that the present invention may be practiced without the specific details. Furthermore, well-known features may be omitted or simplified in order not to obscure the embodiment being described.

Patient interface assemblies and related methods for use in laser surgery systems are provided. While described herein as used in laser eye surgery systems, the patient interface assemblies and methods described herein can be used in any other suitable laser surgery system. In many embodiments, a patient interface assembly is configured to accommodate movement of a patient relative to the laser surgery system while maintaining alignment between an electromagnetic treatment beam emitted by the laser surgery system and the patient.

Figure 1:
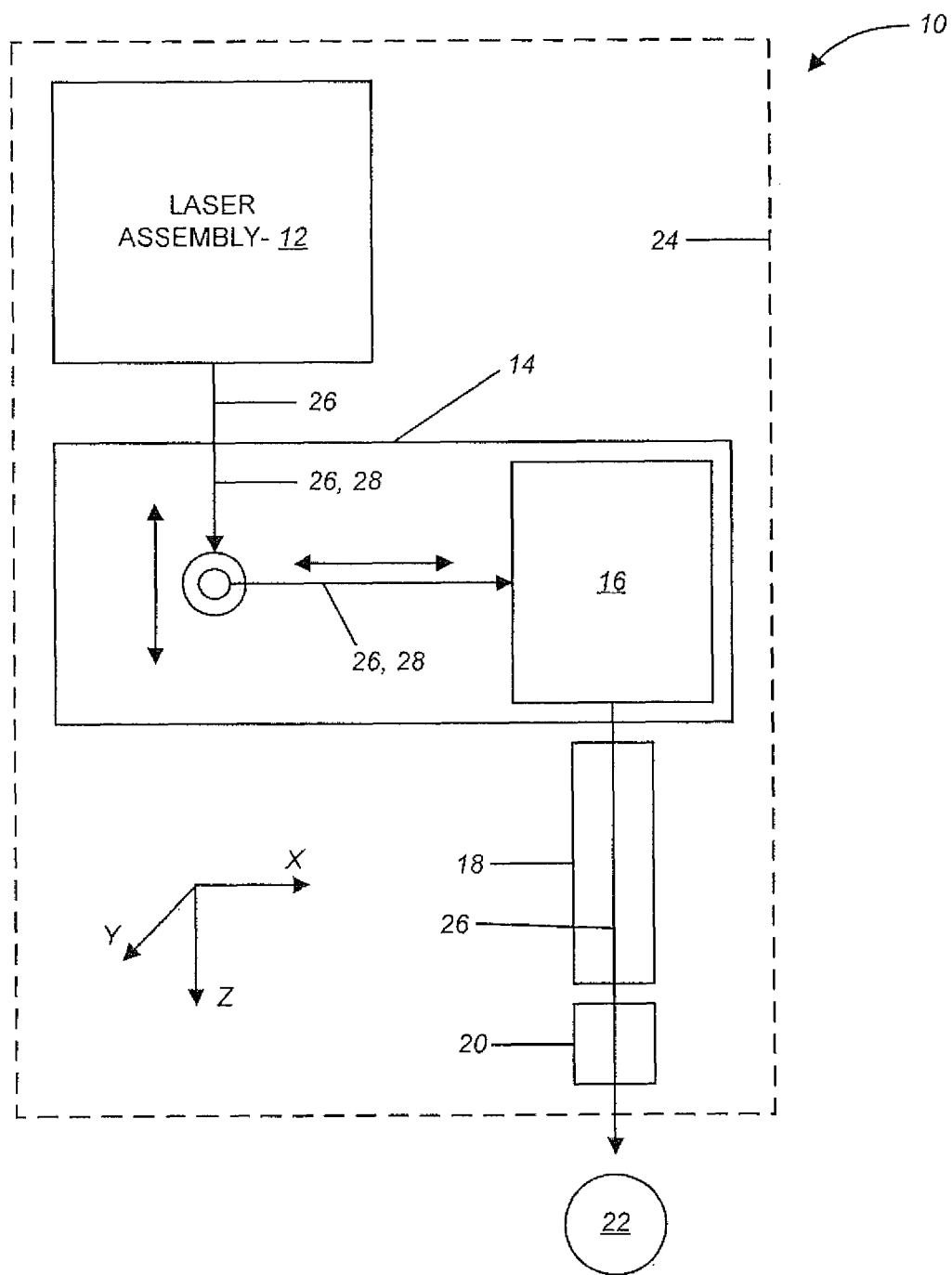
FIG. 1 is a schematic diagram of a laser surgery system, in accordance with many embodiments, in which a patient interface device is coupled to a laser assembly by way of a scanner and free-floating mechanism that supports the scanner.

Referring now to the drawings in which like numbers reference similar elements, FIG. 1 schematically illustrates a laser surgery system 10, in accordance with many embodiments. The laser surgery system 10 includes a laser assembly 12, a free-floating mechanism 14, a scanner 16, an objective lens assembly 18, and a patient interface device 20. The patient interface device 20 is configured to interface with a patient 22. The patient interface device 20 is supported by the objective lens assembly 18. The objective lens assembly 18 is supported by the scanner 16. The scanner 16 is supported by the free-floating mechanism 14. The free-floating mechanism 14 has a portion having a fixed position and orientation relative to the laser assembly 12.

In many embodiments, the patient interface device 20 is configured to interface with an eye of the patient 22. For example, the patient interface device 20 can be configured to be vacuum coupled to an eye of the patient 22 such as described in co-pending U.S. Provisional Patent Application Ser. No. 61/721,693, entitled "Liquid Optical Interface for Laser Eye Surgery System", filed Nov. 2, 2012. The laser surgery system 10 can further optionally include a base assembly 24 that can be fixed in place or repositionable. For example, the base assembly 24 can be supported by a support linkage that is configured to allow selective repositioning of the base assembly 24 relative to a patient and secure the base assembly 24 in a selected fixed position relative to the patient. Such a support linkage can be supported in any suitable manner such as, for example, by a fixed support base or by a movable cart that can be repositioned to a suitable location adjacent to a patient. In many embodiments, the support linkage includes setup joints with each setup joint being configured to permit selective articulation of the setup joint and can be selectively locked to prevent inadvertent articulation of the setup joint, thereby securing the base assembly 24 in a selected fixed position relative to the patient when the setup joints are locked.

In many embodiments, the laser assembly 12 is configured to emit an electromagnetic radiation beam 26. The beam 26 can include a series of laser pulses of any suitable energy level, duration, and repetition rate.

In many embodiments, the laser assembly 12 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to laser pulses having longer durations.

The laser assembly 12 can produce laser pulses having a wavelength suitable to treat and/or image tissue. For example, the laser assembly 12 can be configured to emit an electromagnetic radiation beam 26 such as emitted by any of the laser surgery systems described in copending U.S. Provisional Patent Application Ser. No. 61/722,048, entitled "Laser Eye Surgery System", filed Nov. 2, 2012; U.S. Pat. No. 12,987,069, entitled "Method and System For Modifying Eye Tissue and Intraocular Lenses", filed Jan. 7, 2011. For example, the laser assembly 12 can produce laser pulses having a wavelength from 1020 nm to 1050 nm. For example, the laser assembly 12 can have a diode-pumped solid-state configuration with a 1030 (+/−5) nm center wavelength. As another example, the laser assembly 12 can produce laser pulses having a wavelength 320 nm to 430 nm. For example, the laser assembly 12 can include an Nd:YAG laser source operating at the 3rd harmonic wavelength, 355 nm. The laser assembly 12 can also include two or more lasers of any suitable configuration.

The laser assembly 12 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly and a fixed optical relay to transfer the laser pulses over a distance while accommodating laser pulse beam positional and/or directional variability, thereby providing increased tolerance for component variation.

In many embodiments, the laser assembly 12 has a fixed position relative to the base assembly 24. The beam 26 emitted by the laser assembly 12 propagates along a fixed optical path to the free-floating mechanism 14. The beam 12 propagates through the free-floating mechanism 14 along a variable optical path 28, which delivers the beam 26 to the scanner 16. In many embodiments, the beam 26 emitted by the laser assembly 12 is collimated so that the beam 26 is not impacted by patient movement induced changes in the length of the optical path between the laser assembly 12 and the scanner 16. The scanner 16 is operable to scan the beam 26 (e.g., via controlled variable deflection of the beam 26) in at least one dimension. In many embodiments, the scanner is operable to scan the beam in two dimensions transverse to the direction of propagation of the beam 26 and is further operable to scan the location of a focal point of the beam 26 in the direction of propagation of the beam 26. The scanned beam is emitted from the scanner 16 to propagate through the objective lens assembly 18, through the interface device 20, and to the patient 22.

The free-floating mechanism 14 is configured to accommodate a range of movement of the patient 22 relative to the laser assembly 12 in one or more directions while maintaining alignment of the beam 24 emitted by the scanner 16 with the patient 22. For example, in many embodiments, the free-floating mechanism 14 is configured to accommodate a range movement of the patient 22 in any direction defined by any combination of unit orthogonal directions (X, Y, and Z).

The free-floating mechanism 14 supports the scanner 16 and provides the variable optical path 28, which changes in response to movement of the patient 22. Because the patient interface device 20 is interfaced with the patient 22, movement of the patient 22 results in corresponding movement of the patient interface device 20, the objective lens assembly 18, and the scanner 16. The free-floating mechanism 14 can include, for example, any suitable combination of a linkage that accommodates relative movement between the scanner 16 and the laser assembly 12 and optical components suitably tied to the linkage so as to form the variable optical path 28.

Figure 2:
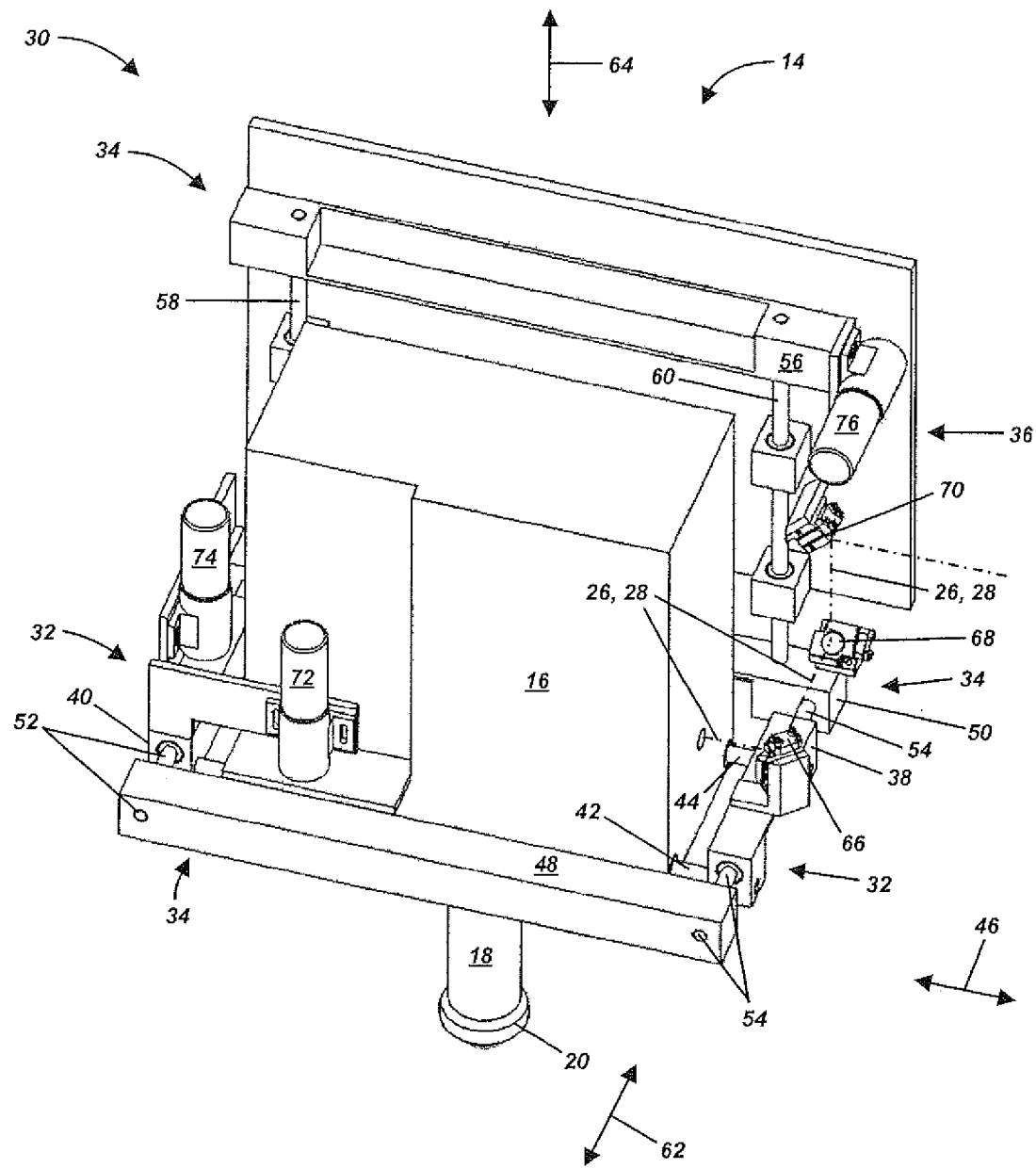
FIG. 2 shows an isometric view of a patient interface assembly, in accordance with many embodiments, that includes a scanner supported by a free-floating mechanism.

FIG. 2 shows an assembly 30 to illustrate an example embodiment of a suitable combination of a linkage that accommodates relative movement between the scanner 16 and the laser assembly 12 and optical components suitably tied to the linkage so as to form the variable optical path 28. The assembly 30 includes an eye interface device 20, the objective lens assembly 18, the scanner 16, and the free-floating mechanism 14. The free-floating mechanism 14 includes a first support assembly 32, a second support assembly 34, and a base assembly 36. The eye interface device 20 is coupled with and supported by the objective lens assembly 18. The objective lens assembly 18 is coupled with and supported by the scanner 16. The combination of the interface device 20, the objective lens assembly 18, and the scanner 16 form a unit that moves in unison in conjunction with movement of the patient.

The first support assembly 32 includes a first end frame 38, a second end frame 40, and transverse rods 42, 44, which extend between and couple to the end frames 38, 40. The transverse rods 42, 44 are oriented parallel to a first direction 46. The scanner 16 is supported by the transverse rods 42, 44 and slides along the rods 42, 44 in response to patient movement parallel to the first direction 46. The transverse rods 42, 44 form part of a linear bearing accommodating patient movement parallel to the first direction 46.

The second support assembly 34 includes a first end frame 48, an intermediate frame 50, transverse rods 52, 54, a second end frame 56, and vertical rods 58, 60. The transverse rods 52, 54 extend between and couple to the first end frame 48 and to the intermediate frame 50. The transverse rods 52, 54 are oriented parallel to a second direction 62, which is at least transverse to and can be orthogonal to the first direction 46. Each of the first and second directions 46, 62 can be horizontal. The first support assembly 32 is supported by the transverse rods 52, 54 and slides along the rods 52, 54 in response to patient movement parallel to the second direction 62. The transverse rods 52, 54 form part of a linear bearing accommodating patient movement parallel to the second direction 62. The vertical rods 58, 60 extend between and couple to the intermediate frame 50 and to the second end frame 56. The vertical rods 58, 60 are oriented parallel to a third direction 64, which is at least transverse to each of first and second directions 46, 62, and can be orthogonal to at least one of the first and second directions 46, 62. The vertical rods 58, 60 form part of a linear bearing accommodating relative movement between the second support assembly 34 and the base assembly 36 parallel to the third direction 64, thereby accommodating patient movement parallel to the third direction 64.

First, second, and third reflectors 66, 68, 70 (e.g., mirrors) are supported by the free-floating mechanism 14 and configured to reflect the electromagnetic radiation beam 26 to propagate along a variable optical path 28. The first reflector 66 is mounted to the first support assembly 32 (to second end frame 42 in the illustrated embodiment). The second reflector 68 is mounted to the second support assembly 34 (to intermediate frame 50 in the illustrated embodiment). The third reflector 70 is mounted to the base assembly 36. In operation, the beam 26 emitted by the laser assembly is deflected by the third reflector 70 so as to propagate parallel to the third direction 64 and be incident upon the second reflector 68. The second reflector 68 deflects the beam 26 so as to propagate parallel to the second direction 62 and be incident upon the first reflector 66. The first reflector 66 deflects the beam 26 so as to propagate parallel to the first direction 46 and into the scanner 16, which then controllably scans and outputs the scanned beam through the objective lens assembly 18 and the eye interface device 20. By propagating the beam 26 parallel to the third direction 64 from the third reflector 70 to the second reflector 68, the length of the corresponding portion of the variable optical path 28 can be varied so as to accommodate relative movement of the patient relative to the third direction 64. By propagating the beam 26 parallel to the second direction 62 from the second reflector 68 to the first reflector 66, the length of the corresponding portion of the variable optical path 28 can be varied so as to accommodate relative movement of the patient relative to the second direction 62. By propagating the beam 26 parallel to the first direction 46 from the first reflector 66 to the scanner 16, the length of the corresponding portion of the variable optical path 28 can be varied so as to accommodate relative movement of the patient relative to the first direction 46.

In the illustrated embodiment, the free-floating mechanism 14 further includes a first solenoid brake assembly 72, a second solenoid brake assembly 74, and a third solenoid brake assembly 76. The solenoid brake assemblies 72, 74, 76 are operable to selectively prevent inadvertent articulation of the free-floating mechanism 14 during initial positioning of the scanner 16 relative to a patient's eye. For example, in the absence of any mechanism for preventing inadvertent articulation of the free-floating mechanism 14, movement of the scanner 16 may induce inadvertent articulation of the free-floating mechanism 14, especially when a user induces movement of the scanner 16 through contact with, for example, the objective lens assembly 18 to move the objective lens assembly 18 into a suitable location relative to the patient. When the laser surgery system 10 is supported by a support linkage mechanism that includes setup joints, preventing inadvertent articulation of the free-floating mechanism 14 can be used to ensure that the initial positioning of the laser surgery system 10 occurs via articulation of the setup joints instead of via articulation of the free-floating mechanism 14.

The first solenoid brake assembly 72 is configured to selectively prevent inadvertent movement between the scanner 16 and the first support assembly 32. Engagement of the first solenoid brake assembly 72 prevents movement of the scanner 16 along the transverse rods 42, 44, thereby preventing relative movement between the scanner 16 and the first support assembly 32 parallel to the first direction 46. When the first solenoid brake assembly 72 is not engaged, the scanner 16 is free to slide along the transverse rods 42, 44, thereby permitting relative movement between the scanner 16 and the first support assembly 32 parallel to the first direction 46. In many embodiments, the free-floating mechanism 14 includes a detent mechanism and/or an indicator that is configured to permit engagement of the first solenoid brake assembly 72 when the scanner 16 is centered relative to its range of travel along the transverse rods 42, 44, thereby ensuring equal range of travel of the scanner 16 in both directions parallel to the first direction 46 when the first solenoid brake assembly 72 is disengaged following positioning of the objective lens assembly 18 relative to the patient.

The second solenoid brake assembly 74 is configured to selectively prevent inadvertent movement between the first support assembly 32 and the second support assembly 34. Engagement of the second solenoid brake assembly 74 prevents movement of the first support assembly 32 along the transverse rods 52, 54, thereby preventing relative movement between the first support assembly 32 and the second support assembly 34 parallel to the second direction 62. When the second solenoid brake assembly 74 is not engaged, the first support assembly 32 is free to slide along the transverse rods 52, 54, thereby permitting relative movement between the first support assembly 32 and the second support assembly 34 parallel to the second direction 62. In many embodiments, the free-floating mechanism 14 includes a detent mechanism and/or an indicator that is configured to permit engagement of the second solenoid brake assembly 74 when the first support assembly 32 is centered relative to its range of travel along the transverse rods 52, 54, thereby ensuring equal range of travel of the first support assembly 32 in both directions parallel to the second direction 62 when the second solenoid brake assembly 74 is disengaged following positioning of the objective lens assembly 18 relative to the patient.

The third solenoid brake assembly 76 is configured to selectively prevent inadvertent movement between the second support assembly 34 and the base assembly 36. Engagement of the third solenoid brake assembly 76 prevents movement of the base assembly 36 along the vertical rods 58, 60, thereby preventing relative movement between the second support assembly 34 and the base assembly 36 parallel to the third direction 64. When the third solenoid brake assembly 76 is not engaged, the base assembly 36 is free to slide along the vertical rods 58, 60, thereby permitting relative movement between the second support assembly 34 and the base assembly 36 parallel to the third direction 64. In many embodiments, the free-floating mechanism 14 includes a detent mechanism and/or an indicator that is configured to permit engagement of the third solenoid brake assembly 76 when the base assembly 36 is centered relative to its range of travel along the vertical rods 58, 60, thereby ensuring equal range of travel of the base assembly 36 in both directions parallel to the third direction 64 when the third solenoid brake assembly 76 is disengaged following positioning of the objective lens assembly 18 relative to the patient.

In an optional embodiment, the third reflector 70 is omitted and the incoming beam 26 is directed to propagate parallel to the third direction 64 and be incident on the second reflector 68. Each of the reflectors 66, 68, 70 can be adjustable in position and/or in orientation and thereby can be adjusted to align the corresponding portions of the variable optical path 28 with the first, second, and third directions 46, 62, and 64, respectively. Accordingly, the use of the third reflector 70 can provide the ability to align the portion of the variable optical path 28 between the third reflector 70 and the second reflector 68 so as to be parallel to the third direction 64 and thereby compensate for relative positional and/or orientation variability between the laser assembly 12 and the free-floating mechanism 14.

In the illustrated embodiment of the assembly 30, the first and second directions 46, 62 can be horizontal and the third direction 64 can be vertical. The free-floating mechanism 14 can also include a counter-balance mechanism coupled with the scanner and configured to inhibit gravity-induced movement of the eye interface device 20 and/or inhibit the transfer of gravity-induced forces from the eye interface device 20 to an eye coupled with the eye interface device 20. For example, a counter-balance mechanism can be employed to apply a counter-balancing vertical force to the second assembly 34, thereby inhibiting or even preventing gravity-induced relative movement between the second assembly 34 and the base assembly 36 and/or inhibiting the transfer of gravity-induced forces from the eye interface device 20 to an eye coupled with the eye interface device 20.

Other suitable variations of the assembly 30 are possible. For example, the scanner 16 can be slidably supported relative to a first support assembly via a vertically-oriented linear bearing. The first support assembly can be slidably supported relative to a second support assembly via a first horizontally-oriented linear bearing. The second support assembly can be slidably supported relative to a base assembly via a second horizontally-oriented linear bearing that is oriented transverse (e.g., perpendicular) to the first horizontally-oriented linear bearing. In such a configuration, a counter-balancing mechanism can be used to apply a counter-balancing force to the scanner 16, thereby inhibiting or even preventing gravity-induced relative movement of the scanner 16 and the eye interface device 20 and/or inhibiting or even preventing the transfer of gravity-induced force from the eye interface device 20 to an eye coupled with the eye interface device 20. The assembly 30 can also incorporate one or more sensors configured to monitor relative position 1) between the scanner 16 and the first support assembly 32, 2) between the first support assembly 32 and the second support assembly 34, and/or 3) between the second support assembly 34 and the base assembly 36.

Figure 3:
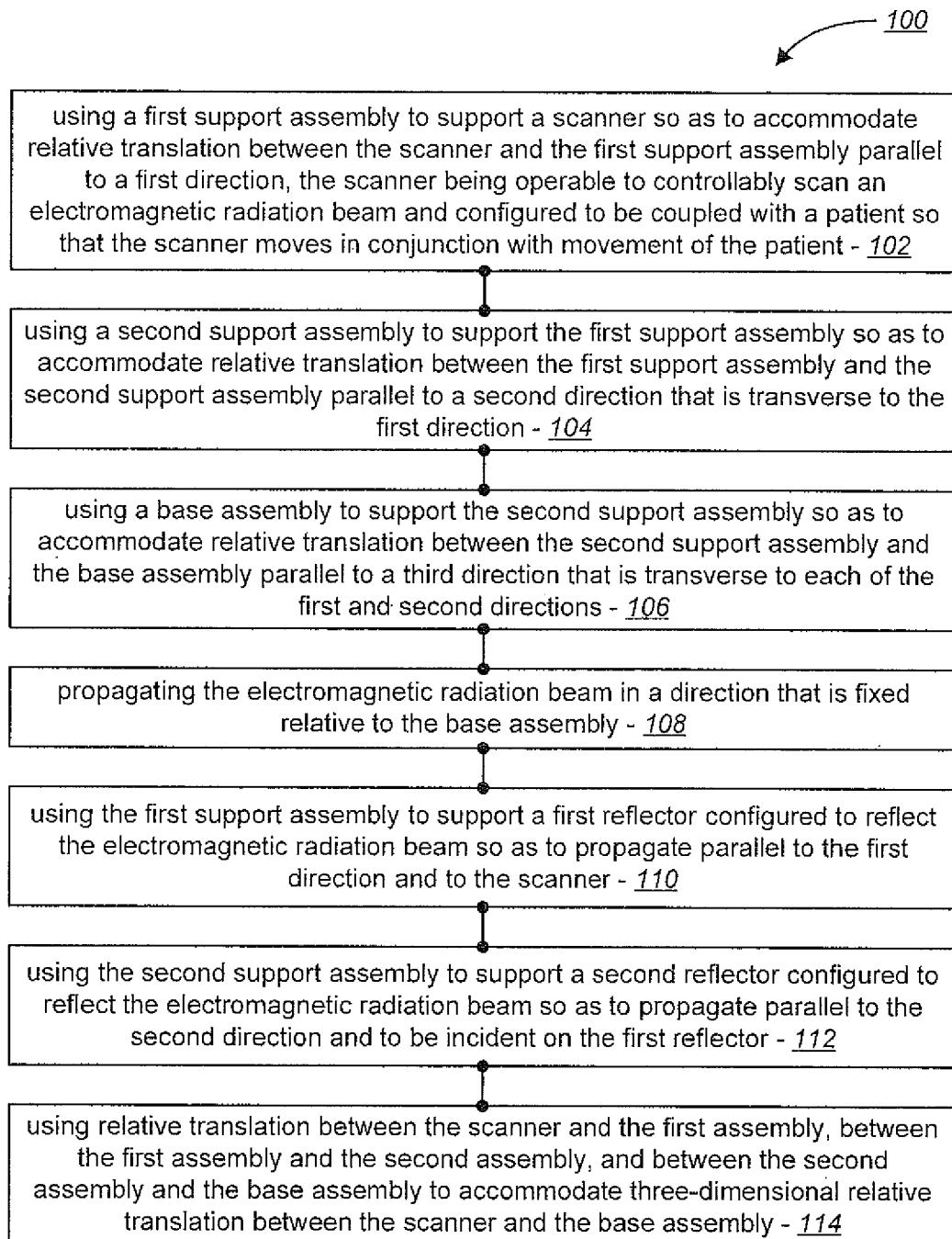
FIG. 3 is a simplified block diagram of acts of a method, in accordance with many embodiments, for accommodating patient movement in a laser surgery system.

FIG. 3 is a simplified block diagram of acts of a method 100, in accordance with many embodiments, of accommodating patient movement in a laser surgery system. Any suitable device, assembly, and/or system described herein can be used to practice the method 100. The method 100 includes using a first support assembly (e.g., first support assembly 32) to support a scanner (e.g., scanner 16) so as to accommodate relative translation between the scanner and the first support assembly parallel to a first direction (e.g., direction 46). The scanner is operable to controllably scan an electromagnetic radiation beam (e.g., beam 26) and configured to be coupled with a patient so that the scanner moves in conjunction with movement of the patient (act 102). A second support assembly (e.g., second support assembly 34) is used to support the first support assembly so as to accommodate relative translation between the first support assembly and the second support assembly parallel to a second direction (e.g., direction 62) that is transverse to the first direction (act 104). A base assembly (e.g., base assembly 36) is used to support the second support assembly so as to accommodate relative translation between the second support assembly and the base assembly parallel to a third direction (e.g., direction 64) that is transverse to each of the first and second directions (act 106). The electromagnetic radiation beam is propagated in a direction that is fixed relative to the base assembly (act 108). The first support assembly is used to support a first reflector (e.g., first reflector 66) configured to reflect the electromagnetic radiation beam so as to propagate parallel to the first direction and to the scanner (act 110). The second support assembly is used to support a second reflector (e.g., second reflector 68) configured to reflect the electromagnetic radiation beam so as to propagate parallel to the second direction and to be incident on the first reflector (act 112). Relative translation between the scanner and the first assembly, between the first assembly and the second assembly, and between the second assembly and the base assembly is used to accommodate three-dimensional relative translation between the scanner and the base assembly (act 114).

FIG. 4 is a simplified block diagram of additional aspects and/or optional acts that can be accomplished as part of the method 100. For example, the method 100 can include using the base assembly to support a third reflector (e.g., third reflector 70) configured to reflect the electromagnetic radiation beam to propagate parallel to the third direction and to be incident on the second reflector (act 116). The method 100 can include operating the scanner to scan the electromagnetic radiation beam in at least two dimensions (act 118). The method 100 can include focusing the electromagnetic radiation beam to a focal point (act 120). The method 100 can include operating the scanner to scan the focal point in three dimensions (act 122). The method 100 can include using a counter-balance mechanism to inhibit gravity-induced movement of the scanner and/or to inhibit transfer of gravity-induced force to an eye coupled with the scanner (act 124). The method 100 can include monitoring a relative position of at least one of the group consisting of (1) between the scanner and the first support assembly, (2) between the first support assembly and the second support assembly, and (3) between the second support assembly and the base assembly (act 126). The method 100 can include inhibiting relative movement during positioning of the scanner relative to the patient between at least one of (1) the scanner and the first support assembly, (2) the first support assembly and the second support assembly, and (3) the second support assembly and the base assembly (act 128).

Figure 5:
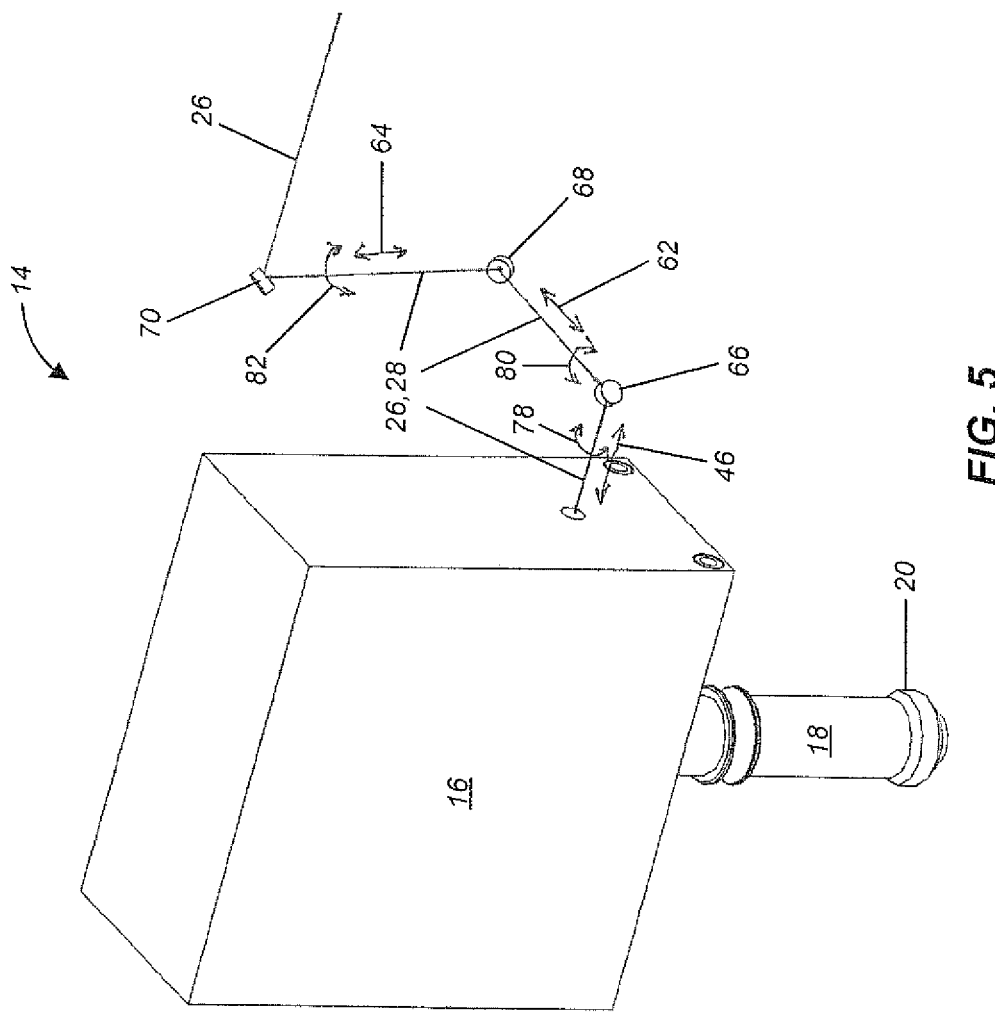
FIG. 5 schematically illustrates relative movements that can be used in a patient interface assembly, in accordance with many embodiments, that includes a scanner supported by a free-floating mechanism.

FIG. 5 schematically illustrates relative movements that can be used in the free-floating mechanism 14 that can be used to accommodate patient movement, in accordance with many embodiments. The free-floating mechanism 14 includes the first reflector 66, the second reflector 68, and the third reflector 70. In many embodiments, the free-floating mechanism 14 includes a linkage assembly (not shown) that is configured to permit certain relative movement between the scanner 16 and the first reflector 66, between the first reflector 66 and the second reflector 68, and between the second reflector 68 and the third reflector 70 so as to consistently direct the electromagnetic radiation beam 26 to the scanner 16 while accommodating three-dimensional relative movement between the patient interface device 20 and the laser assembly used to generate the electromagnetic radiation beam 26. For example, similar to the embodiment of the free-floating mechanism 14 illustrated in FIG. 2, a free-floating mechanism 14 can be configured such that the scanner 16 is supported by a first support assembly such that the scanner is free to translate relative to the first support assembly parallel to the first direction 46, thereby maintaining the location and orientation of the beam 26 between the first reflector 66 and the scanner 16. Likewise, the first support assembly can be supported by a second support assembly such that the first support assembly is free to translate relative to the second support assembly parallel to a second direction 62, thereby maintaining the location and orientation of the beam 26 between the second reflector 68 and the first reflector 66. And the second support assembly can be supported by a base assembly such that the second support assembly is free to translate relative to the base assembly parallel to a third direction 64, thereby maintaining the location and orientation of the beam 26 between the third reflector 70 and the second reflector 68.

The free-floating mechanism 14 can also employ one or more relative rotations so as to maintain the location and orientation of path segments of the beam 26. For example, the scanner 16 can be supported by a first support assembly such that the scanner is free to undergo a rotation 78 relative to the first support assembly about an axis coincident with the path segment of the beam 26 between the first reflector 66 and the scanner 16, thereby maintaining the location and orientation of the beam 26 between the first reflector 66 and the scanner 16. Likewise, the first support assembly can be supported by a second support assembly such that the first support assembly is free to undergo a rotation 80 relative to the second support assembly about an axis coincident with the path segment of the beam 26 between the second reflector 68 and the first reflector 66, thereby maintaining the location and orientation of the beam 26 between the second reflector 68 and the first reflector 66. And the second support assembly can be supported by a base assembly such that the second support assembly is free to undergo a rotation 82 relative to the base assembly about an axis coincident with the path segment of the beam 26 between the third reflector 70 and the second reflector 68, thereby maintaining the location and orientation of the beam 26 between the third reflector 70 and the second reflector 68.

The free-floating mechanism 14 can also employ any suitable combination of relative translations and relative rotations so as to maintain the location and orientation of path segments of the beam 26. For example, with respect to the configuration illustrated in FIG. 5, the free-floating mechanism 14 can employ relative translation parallel to the second direction 62, relative translation parallel to the third direction 64, and relative rotation 82, thereby allowing three-dimensional movement of the patient interface 20 relative to the laser assembly used to generate the electromagnetic radiation beam 26, and thereby accommodating patient movement.

Figure 6A:
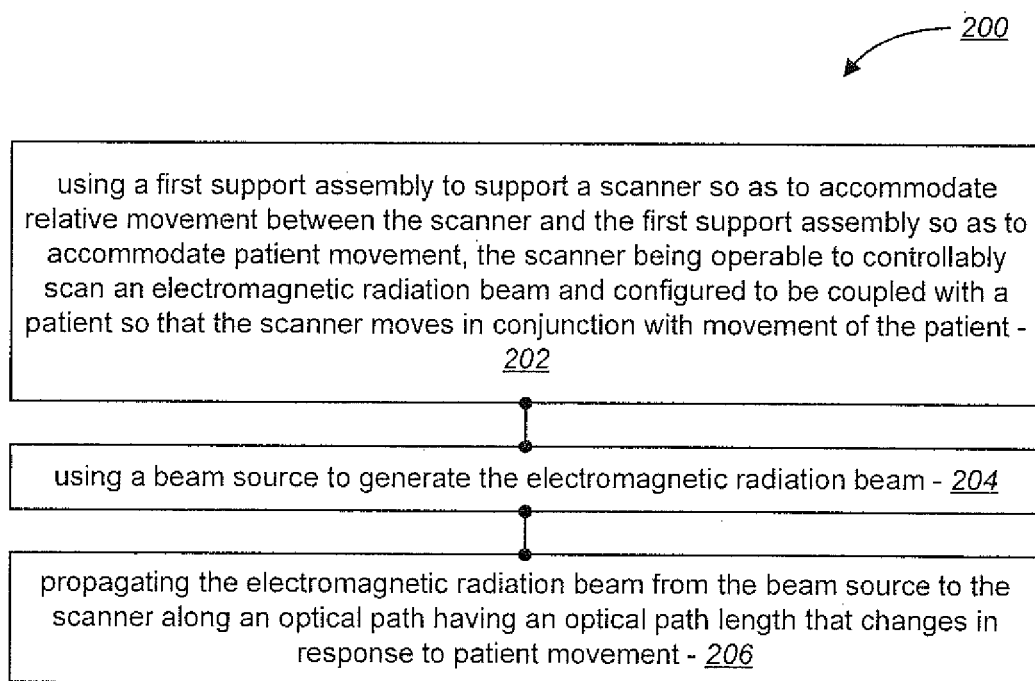
FIG. 6A is a simplified block diagram of acts of another method, in accordance with many embodiments, for accommodating patient movement in a laser surgery system.

FIG. 6A is a simplified block diagram of acts of a method 200, in accordance with many embodiments, of accommodating patient movement in a laser surgery system. Any suitable device, assembly, and/or system described herein can be used to practice the method 200. The method 200 includes using a first support assembly to support a scanner so as to accommodate relative movement between the scanner and the first support assembly so as to accommodate patient movement. The scanner is operable to controllably scan an electromagnetic radiation beam and configured to be coupled with a patient so that the scanner moves in conjunction with movement of the patient (act 202). The method 200 includes using a beam source to generate the electromagnetic radiation beam (act 204). The method 200 includes propagating the electromagnetic radiation beam from the beam source to the scanner along an optical path having an optical path length that changes in response to patient movement (act 206).

FIG. 6B is a simplified block diagram of additional aspects and/or optional acts that can be accomplished as part of the method 200. For example, the method 200 can include using a second support assembly to support the first support assembly so as to accommodate relative movement between the first support assembly and the second support assembly so as to accommodate patient movement (act 208). The method 200 can include using the first support assembly to support a first reflector configured to reflect the electromagnetic radiation beam so as to propagate to the scanner along a portion of the optical path (act 210). The method 200 can include using a base assembly to support the second support assembly so as to accommodate relative movement between the second support assembly and the base assembly so as to accommodate patient movement (act 212). The method 200 can include using the second support assembly to support a second reflector configured to reflect the electromagnetic radiation beam to propagate along a portion of the optical path so as to be incident on the first reflector (act 214). The method 200 can include using the base assembly to support a third reflector configured to reflect the electromagnetic radiation beam to propagate along a portion of the optical path so as to be incident on the second reflector (act 216). The method 200 can include monitoring at least one of a relative position and a relative orientation of at least one of the group consisting of (1) between the scanner and the first support assembly, (2) between the first support assembly and the second support assembly, and (3) between the second support assembly and the base assembly (act 218). The method 200 can include inhibiting relative movement during positioning of the scanner relative to the patient between at least one of (1) the scanner and the first support assembly, (2) the first support assembly and the second support assembly, and (3) the second support assembly and the base assembly (act 220).

Figure 7:
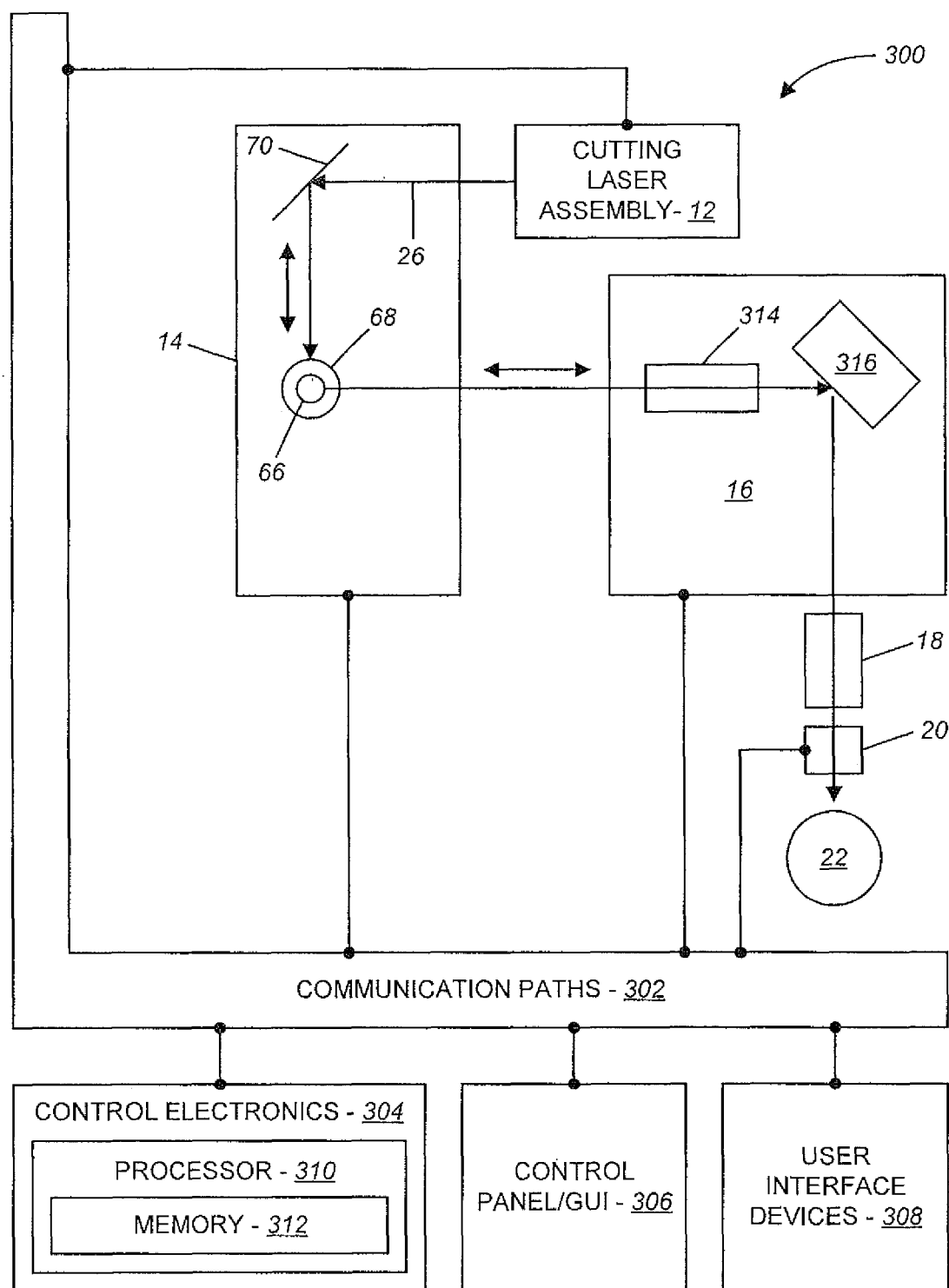
FIG. 7 is a schematic diagram of a laser surgery system, in accordance with many embodiments, in which an eye interface device is coupled to a laser assembly by way of a scanner and free-floating mechanism that supports the scanner.

FIG. 7 schematically illustrates a laser surgery system 300, in accordance with many embodiments. The laser surgery system 300 includes the laser assembly 12, the free-floating mechanism 14, the scanner 16, the objective lens assembly 18, the patient interface 20, communication paths 302, control electronics 304, control panel/graphical user interface (GUI) 306, and user interface devices 308. The control electronics 304 includes processor 310, which includes memory 312. The patient interface 20 is configured to interface with a patient 22. The control electronics 304 is operatively coupled via the communication paths 302 with the laser assembly 12, the free-floating mechanism 14, the scanner 16, the control panel/GUI 306, and the user interface devices 308.

The free-floating mechanism 14 can be configured as illustrated in FIG. 2 to include, for example, the first reflector 66, the second reflector 68, and the third reflector 70. Accordingly, the free-floating mechanism 14 can be configured to accommodate movement of the patient 22 relative to the laser assembly 12 in any direction resulting from any combination of three orthogonal unit directions.

The scanner 16 includes a z-scan device 314 and an xy-scan device 316. The laser surgery system 300 is configured to focus the electromagnetic radiation beam 26 to a focal point that is scanned in three dimensions. The z-scan device 314 is operable to vary the location of the focal point in the direction of propagation of the beam 26. The xy-scan device 316 is operable to scan the location of the focal point in two dimensions transverse to the direction of propagation of the beam 26. Accordingly, the combination of the z-scan device 314 and the xy-scan device 316 can be operated to controllably scan the focal point of the beam in three dimensions, including within a tissue of the patient 22 such as within an eye tissue of the patient 22. As described above with respect to assembly 30, the scanner 16 is supported by the free-floating mechanism 14, which accommodates patient movement induced movement of the scanning device relative to the laser assembly 12 in three dimensions.

The patient interface 20 is coupled to the patient 22 such that the patient interface 20, the objective lens 18, and the scanner 16 move in conjunction with the patient 22. For example, in many embodiments, the patient interface 20 employs a suction ring that is vacuum attached to an eye of the patient 20. The suction ring can be coupled with the patient interface 20, for example, using vacuum to secure the suction ring to the patient interface 20.

The control electronics 304 controls the operation of and/or can receive input from the laser assembly 12, the free-floating assembly 14, the scanner 16, the patient interface 20, the control panel/GUI 306, and the user interface devices 308 via the communication paths 302. The communication paths 302 can be implemented in any suitable configuration, including any suitable shared or dedicated communication paths between the control electronics 304 and the respective system components.

The control electronics 304 can include any suitable components, such as one or more processor, one or more field-programmable gate array (FPGA), and one or more memory storage devices. In many embodiments, the control electronics 304 controls the control panel/GUI 306 to provide for pre-procedure planning according to user specified treatment parameters as well as to provide user control over the laser eye surgery procedure.

The control electronics 304 can include a processor/controller 310 that is used to perform calculations related to system operation and provide control signals to the various system elements. A computer readable medium 312 is coupled to the processor 310 in order to store data used by the processor and other system elements. The processor 310 interacts with the other components of the system as described more fully throughout the present specification. In an embodiment, the memory 312 can include a look up table that can be utilized to control one or more components of the laser system surgery system 300.

The processor 310 can be a general purpose microprocessor configured to execute instructions and data, such as a Pentium processor manufactured by the Intel Corporation of Santa Clara, California. It can also be an Application Specific Integrated Circuit (ASIC) that embodies at least part of the instructions for performing the method in accordance with the embodiments of the present disclosure in software, firmware and/or hardware. As an example, such processors include dedicated circuitry, ASICs, combinatorial logic, other programmable processors, combinations thereof, and the like.

The memory 312 can be local or distributed as appropriate to the particular application. Memory 312 can include a number of memories including a main random access memory (RAM) for storage of instructions and data during program execution and a read only memory (ROM) in which fixed instructions are stored. Thus, the memory 312 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 308 can include any suitable user input device suitable to provide user input to the control electronics 304. For example, the user interface devices 308 can include devices such as, for example, a touch-screen display/input device, a keyboard, a footswitch, a keypad, a patient interface radio frequency identification (RFID) reader, an emergency stop button, and a key switch.

Any suitable laser surgery system can be suitably modified to employ an electromagnetic beam scanner that is supported by a free-floating mechanism as disclosed herein. For example, copending U.S. provisional patent application Ser. No. 61/722,048 filed Nov. 11, 2012, describes a laser eye surgery system that includes beam scanning components that form part of a shared optical assembly used to scan a treatment beam, an optical coherence tomography (OCT) measurement beam, and an alignment beam. Using the approaches described herein, such beam scanning components can be supported from a free-floating mechanism so as to accommodate patient movement as described herein.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A patient interface assembly for a laser eye surgery system, the patient interface assembly comprising:
   an eye interface device configured to interface with an eye of a patient;
   a scanner configured to be coupled with the eye interface device and operable to scan an electromagnetic radiation beam in at least two dimensions in an eye interfaced with the eye interface device, the scanner and the eye interface device configured to move in conjunction with movement of the eye;
   a first support assembly that supports the scanner so as to accommodate relative movement between the scanner and the first support assembly parallel to a first direction so as to accommodate the movement of the eye;
   a first brake assembly configured to brake movement between the scanner and the first support assembly during positioning of the scanner relative to the patient; and
   a beam source that generates the electromagnetic radiation beam, wherein the electromagnetic radiation beam propagates from the beam source to the scanner along an optical path having an optical path length that varies in response to the movement of the eye.

2. The patient interface assembly of claim 1, further comprising:
   a second support assembly that supports the first support assembly so as to accommodate relative movement between the first support assembly and the second support assembly so as to accommodate the movement of the eye; and
   a first reflector supported by the first support assembly and configured to reflect the electromagnetic radiation beam to propagate to the scanner along a portion of the optical path.

3. The patient interface assembly of claim 2, further comprising:
   a base assembly that supports the second support assembly so as to accommodate relative movement between the second support assembly and the base assembly so as to accommodate the movement of the eye; and
   a second reflector supported by the second support assembly and configured to reflect the electromagnetic radiation beam to propagate along a portion of the optical path so as to be incident on the first reflector.

4. The patient interface assembly of claim 3, wherein:
   the relative movement between the scanner and the first support assembly is a translation in the first direction;
   the relative movement between the first support assembly and the second support assembly is a translation in a second direction that is transverse to the first direction; and
   the relative movement between the second support assembly and the base assembly is a translation in a third direction that is transverse to each of the first and second directions.

5. The patient interface assembly of claim 4, wherein:
   the second direction is perpendicular to the first direction; and
   the third direction is perpendicular to each of the first and second directions.

6. The patient interface assembly of claim 4, further comprising a counter-balance mechanism coupled with the scanner and configured to inhibit at least one of gravity-induced movement of the scanner in the vertical direction and transfer of gravity-induced force to the eye.

7. The patient interface assembly of claim 6, wherein the third direction is vertically oriented and each of the first and second directions is horizontally oriented.

8. The patient interface assembly of claim 3, wherein at least one of the relative movement between the scanner and the first support assembly, the relative movement between the first support assembly and the second support assembly, and the relative movement between the second support assembly and the base assembly is a relative rotation.

9. The patient interface assembly of claim 3, further comprising a third reflector supported by the base assembly and configured to reflect the electromagnetic radiation beam to propagate along a portion of the optical path so as to be incident on the second reflector.

10. The patient interface assembly of claim 3, further comprising at least one sensor configured to monitor relative position of at least one of the group consisting of between the scanner and the first support assembly, between the first support assembly and the second support assembly, and between the second support assembly and the base assembly.

11. The patient interface assembly of claim 3, further comprising a third brake assembly configured to brake movement between the second support assembly and the base assembly during positioning of the scanner relative to the patient.

12. The patient interface assembly of claim 11, wherein the third brake assembly is a third solenoid brake assembly.

13. The patient interface assembly of claim 2, further comprising a second brake assembly configured to brake movement between the first support assembly and the second support assembly during positioning of the scanner relative to the patient.

14. The patient interface assembly of claim 13, wherein the second brake assembly is a second solenoid brake assembly.

15. The patient interface assembly of claim 1, wherein the scanner is operable to scan the electromagnetic radiation beam in at least two dimensions.

16. The patient interface assembly of claim 1, wherein the scanner is operable to: focus the electromagnetic radiation beam to a focal point; and scan the focal point in three dimensions.

17. The patient interface assembly of claim 1, wherein the electromagnetic radiation beam comprises a series of laser pulses configured to modify eye tissue.

18. The patient interface assembly of claim 1, further comprising an objective lens assembly disposed between and coupled with the scanner and the eye interface device, the electromagnetic radiation beam propagating from the scanner to pass through the objective lens assembly and then from the objective lens assembly through the eye interface device.

19. The patient interface assembly of claim 1, wherein the scanner comprises a z-scan device and an xy-scan device, the z-scan device being operable to change a depth of the focal point in the eye, the xy-scan device being operable to scan the focal point in two dimensions transverse to the propagation direction of the electromagnetic radiation beam.

20. The patient interface assembly of claim 1, wherein the first brake assembly is a first solenoid brake assembly.

* * * * *